United States Patent
Cochran et al.

(10) Patent No.: US 7,227,166 B2
(45) Date of Patent: Jun. 5, 2007

(54) SYSTEM AND METHOD FOR ASSOCIATING CONTAINER DEFECT INFORMATION TO A SPECIFIC PATH OF MANUFACTURING

(75) Inventors: Don W. Cochran, Novelty, OH (US); Dennis S. Bradley, Twinsburg, OH (US); Steven D. Cech, Aurora, OH (US); Frederick F. Awig, II, Lyndhurst, OH (US); Terry L. Graves, Wadsworth, OH (US); Thomas H. Palombo, Akron, OH (US); Michael L. Yoder, Wadsworth, OH (US)

(73) Assignee: Pressco Technology Inc., Cleveland, OH (US)

( * ) Notice: Subject to any disclaimer, the term of this patent is extended or adjusted under 35 U.S.C. 154(b) by 42 days.

(21) Appl. No.: 10/970,780

(22) Filed: Oct. 21, 2004

(65) Prior Publication Data

US 2005/0174571 A1 Aug. 11, 2005

Related U.S. Application Data

(63) Continuation-in-part of application No. PCT/US03/35559, filed on Nov. 7, 2003.

(60) Provisional application No. 60/425,023, filed on Nov. 8, 2002.

(51) Int. Cl.
*G01N 21/88* (2006.01)
*G01N 21/90* (2006.01)
*G01N 21/00* (2006.01)

(52) U.S. Cl. .................. 250/559.45; 250/223 B; 356/240.1

(58) Field of Classification Search ........... 250/559.45, 250/223 B, 559.46, 559.47, 559.48, 559.49; 356/240.1, 237.1, 239.4
See application file for complete search history.

(56) References Cited

U.S. PATENT DOCUMENTS 5,699,152 A * 12/1997 Fedor et al. ............. 356/240.1
5,926,556 A * 7/1999 Douglas et al. ............ 382/142

* cited by examiner

*Primary Examiner*—Georgia Epps
*Assistant Examiner*—Don Williams
(74) *Attorney, Agent, or Firm*—Fay Sharpe LLP

(57) ABSTRACT

This application relates to an apparatus and method for automated inspection of formed metal containers. More specifically, it pertains to the use of machine vision systems to identify and correlate manufacturing defects occurring in formed food and beverage containers to specific manufacturing paths or sources of origin (e.g., body makers) used in the container forming process. The disclosed invention is enabled by the placement of a machine-readable code on specific portions of the can body during the forming process and the use of machine vision reading techniques.

23 Claims, 12 Drawing Sheets

SYSTEM AND METHOD FOR ASSOCIATING CONTAINER DEFECT INFORMATION TO A SPECIFIC PATH OF MANUFACTURING

This application is a continuation-in-part of PCT International Application No. PCT/US2003/035559, filed Nov. 7, 2003 and published in English on May 27, 2004 (International Publication Number WO 2004/044550 A2) (the entire disclosure of which is incorporated herein by reference), which claims priority to and the benefit of U.S. Provisional Application Ser. No. 60/425,023, filed Nov. 8, 2002, the entire disclosure of which is incorporated herein by reference.

FIELD OF THE INVENTION

The present invention relates to a system and method for correlating container defect information to a specific can body maker. More particularly, the invention is directed toward providing a container code formed in the surface of a metal container to identify the machine (e.g. body maker) or press from which the container was produced. The code preferably comprises a fiducial, or reference, marker and suitable additional code to produce an adequate number of codes necessary to identify machines or presses of origin. The codes can then be used during inspection to determine a path of manufacturing, or a source of origin (e.g., originating machine), of the particular containers and accumulate quality information relative to the sources of origin of those containers.

BACKGROUND

By way of background, the use of machine vision systems to inspect the quality of manufactured containers is well known in the art. For example, U.S. Pat. No. 4,882,498 entitled "Pulsed-Array Video Inspection Lighting System" discloses the use of an engineered solid-state illuminator in automated container inspection systems, an improvement to the prior art. Additionally, the extension of automated inspection equipment to include the function of correlating container defect information to specific machine entities used in the manufacturing process is evident in the existing art. As an example, U.S. Pat. No. 5,591,462 entitled "Bottle Inspection Along Molder Transport Path" describes an inspection system for molded plastic or PET containers that identifies container defects and allows those defects to be directly related to a machine entity associated with the containers formation. In this system, container defects can be correlated to the mold cavity, machine transfer arm, or machine spindle used to form a specific bottle. This invention achieves the correlation function by way of its close physical coupling to the manufacturing process. The vision system is installed within the bottle molder and a series of proximity or photo-eye sensors are used by the inspection system to keep track of bottles and the machine entities used to form or handle them.

Also in the area of automated inspection of molded containers, U.S. Pat. No. 5,926,556 entitled "Systems and Methods for Identifying a Molded Container" describes a system wherein a machine-readable code is included in the bottom portion of a molded container during the process of container formation. The code uniquely identifies the mold of origin of the container. This machine-readable code is viewed downstream of the molding operations by an automated inspection system after they have been serialized by the material handling system used in a particular plant into a single randomized stream of containers. This prior patent relates specifically to a system for molded containers and contains no specific provision for integrating the code reading function of a machine vision system, for reading codes stamped in metal containers, with a parallel defect detection functionality. The codes disclosed by the prior patent do not include a fiducial. Also, because molded containers are described in this prior patent, there is no provision for determining the source of origin of the container relative to different machines, as opposed to mold cavities, that form the containers.

The present invention addresses these concerns and others.

SUMMARY OF THE INVENTION

The present invention relates to a system and method for correlating container defect information to a specific can body maker.

It is an object of this invention to provide a system and method of identifying and correlating to machine entities manufacturing defects occurring in metal food and beverage containers.

More specifically, it is an object of this invention to provide a system and method of identifying and correlating container defect information to the specific body maker or deep drawing/ironing press used to form a specific container. The manner in which the machine entry-of-origin is to be determined is via a unique machine-readable code formed into a chime area of the bottom surface of the food or beverage container during its formation.

Another object of the invention is to implement a machine vision system in a manner that is both cost-effective and spatially efficient to facilitate deployment within the existing facilities of can forming operations.

Therefore, in one aspect of the invention, the system comprises a conveyor operative to convey a metal container having formed in a chime area surface thereof a code, the code being unique to a source of origin of the metal containers, an inspection zone into which the metal container is conveyed, an illuminator operative to illuminate the metal container in the inspection zone, an imaging system operative to acquire information on defects and the code and a processor operative to process the information on the defects and the code to generate quality status information relating quality of the metal container to a path of manufacturing, or a source of origin, of the metal container.

In another aspect of the invention, the code is visible on an inside surface of the container and less visible on the outer surface.

In another aspect of the invention, the code is formed in the chime area of the metal container by a body maker.

In another aspect of the invention, the imaging system is operative to inspect the defects at a first exposure level and to inspect the code at a second exposure level.

In another aspect of the invention, the imaging system comprises a beam splitter, a lens and a camera to determine defects and the code by separating reflective light generated by the illuminator into two separate images or channels.

In another aspect of the invention, the imaging system uses spectral filtering to separate a received image into multiple video images or channels.

In another aspect of the invention, the imaging system comprises a high-speed camera and a lens to sequentially acquire a defect attribute image and a code image.

In another aspect of the invention, the imaging system comprises multiple cameras to simultaneously acquire a defect attribute image and a code image.

In another aspect of the invention, the method comprises forming a code in a chime area surface of a metal container, the code being unique to a source of origin or the flow path through the manufacturing process of the metal container, conveying the metal container into an inspection zone, illuminating the metal container in the inspection zone, inspecting the metal container to determine defects in the container, inspecting the metal container to determine the code and accumulating quality status control information based on the defects and the code.

In another aspect of the invention, the stamping of the code is designed such that the forming technique facilitates making the code more visible on the inside surface but less visible on the outside surface of the container. Some manufacturers of containers would prefer that there were minimal or no visibility on the outside surface.

In another aspect of the invention, the forming comprises using press-specific die sets so that the specific manufacturing path that a can followed through the manufacturing plant can later be determined by the unique marking that is put in the can by the unique code that is put in the can. The manufacturing path in most contemporary can plants have a body-maker press mated with a trimmer. The identification, by way of the unique code as to which body-maker press formed the can, also identifies the trimmer that trimmed the can.

In another optional aspect of the invention, inspecting the metal container for defects comprises inspecting at a first illumination exposure level and inspecting the metal container for the code comprises inspecting at a second illumination exposure level. This can be very useful when the optimal illumination is different for each inspection type that may be desirously performed on a can.

In another aspect of the invention, inspecting of the container for defects and the inspecting of the container for the code comprises using spectral filtering to separate a received image into multiple video channels.

In another aspect of the invention, the inspecting to determine defects and the inspecting to determine the code comprises using at least one high-speed camera and a lens to simultaneously or sequentially acquire a defect attribute image and a code image.

In another aspect of the invention, the inspecting to determine defects and the inspecting to determine the code comprises separating reflected light resulting from the illuminating into two separate channels using a beam splitter.

In another aspect of the invention, the stamping comprises using the appropriate tooling in a body maker in order to form the code marks in the can.

In another aspect of the invention, the system comprises means for accomplishing the method according to the present invention.

An advantage of the present invention is that it allows container defect information to be associated to its source of origin so that process correction or improvements may be efficiently accomplished.

Another advantage of the present invention is that it allows correlated defect inspection to be performed in a more cost-effective manner.

Another advantage of the present invention is that it uses the same machine vision system(s) to perform both defect attribute detection and container code processing functions for every container that passes through the line.

Another advantage of the invention is to provide a more distinctive mark that can be readily decoded and interpreted by the machine vision system but, in some forms, is still human readable.

Another advantage of the invention is that the code's small size and centered location will minimize illumination artifacts visible off the container sidewalls while not materially compromising the structural integrity of the container.

Another advantage of the invention is that the code can be easily decoded and interpreted when present at any arbitrary rotational angle to the system's imager or camera.

Another advantage of the system is the ability to "close the loop" to alert a human operator as to how to correct the manufacturing process.

Another advantage of the system is the ability to "close the loop" to correct the manufacturing process automatically.

Another advantage of the invention is the ability to show and communicate the correlated defect attribute information in a wide range of venues and formats to be easily understood and quickly utilized.

Yet another advantage of the system is to correlate defects or problems to the correct trimmer machine.

Further scope of the applicability of the present invention will become apparent from the detailed descriptions provided below. It should be understood, however, that the detailed descriptions and specific examples, while indicating preferred embodiments of the invention, are given by way of illustration only, since various changes and modifications within the spirit and scope of the invention will become apparent to those skilled in the art.

DETAILED DESCRIPTION OF THE DRAWINGS

The present invention exists in the construction, arrangement, and combination of the various parts of the device, and steps of the method, whereby the objects contemplated are attained as hereinafter more fully set forth and illustrated in the accompanying drawings which:

DETAILED DESCRIPTION OF THE INVENTION

The present invention is directed to an apparatus and method for using machine vision systems to identify defect information related to a formed metal container and then associating that defect information to the container's body maker, trimmer or other machinery in the manufacturing path through the factory. The disclosed invention consists of modifying the die sets used to form the bottom portion of a two-piece food or beverage container to include a unique surface relief pattern or code. The coded marks can be either concave or convex in the bottom of the container and can be obtained by so modifying the doming punch accordingly. The code design or pattern is preferably chosen so as to facilitate unambiguous detection and decoding operations by a machine vision system. Preferably, the code provides good visual contrast to the machine vision system, is decodable by the system using a minimum of processing time, does not significantly interfere with the ability of the machine vision system to detect defects that are present, does not in any way interfere with the form, fit, or function of the container, is readable by humans in at least some forms and is inexpensive to retrofit into existing doming punches or dies. Once encoded in this fashion, containers formed by multiple, parallel-operating body makers or presses can be serialized into a single-file, high-speed conveyance line as is typical at many points within plants. At this stage of the manufacturing process, machine vision systems are typically used to perform high-speed defect attribute inspection on the serial can stream. It is the intention of this invention to, at this same inspection station but preferably at a different illumination exposure level, through direct imaging techniques determine the identifying container code indicating its original body maker or press of origin. Through this information, the trimmer of origin can also be determined and corresponding defects can be tracked. This, then, allows container defect information to be correlated to its manufacturing path or source of origin so that process correction or improvements may be efficiently accomplished.

Figure 1:
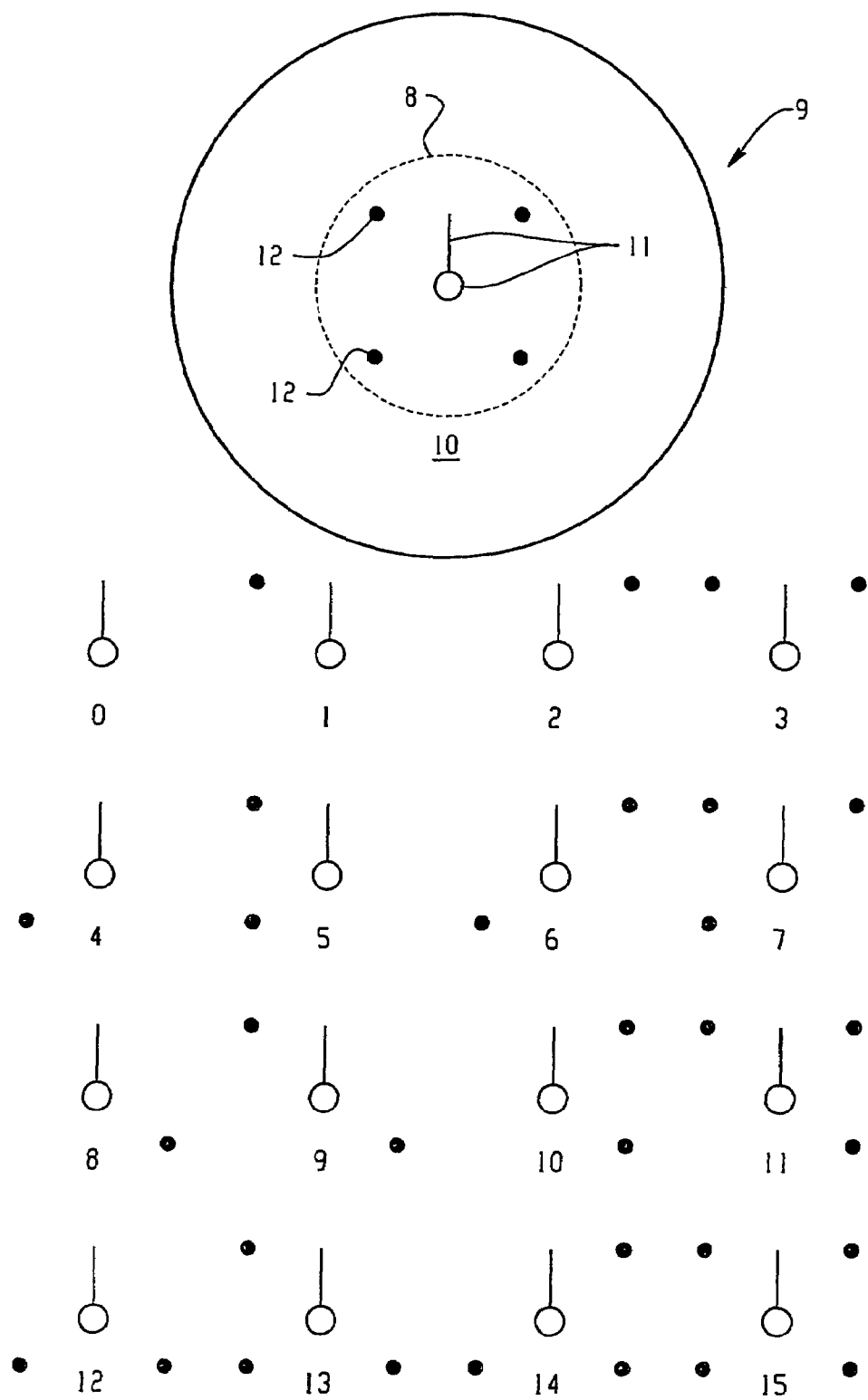
FIG. 1 is a diagram showing a candidate machine-readable code according to the present invention.

Referring now to the drawings wherein the showings are for the purpose of illustrating preferred embodiments of the invention only and not for limiting the same, FIG. 1 shows a candidate machine-readable code according to the present invention. This example code consists of a fiducial element 11 that is used to locate and orient on a 4-bit binary code composed of a rectangular pattern of up to four dots 12. Also illustrated in FIG. 1 is a top view of a doming punch 9 having the example code 10 formed thereon. The code 10, or other codes, are formed on the doming punch in manners that will be apparent to those skilled in the art. It is to be understood that a doming punch is shown as an example. Other stamping and impressing hardware may be implemented. Of course, it should also be understood that such a doming punch (or other hardware) will typically be included within machinery to form metal containers. Although not drawn to scale, the doming punch 9 has the code 10 formed in an area 8 (shown by the dashed circle for illustration purposes) that corresponds preferably to an axially centered region 24 of the dome of the container (which is described in FIG. 2). As a result, where the doming punch stamps the code in the container, the code is preferably totally contained within the axially centered region in the dome. Preferably, this region is circumscribed by a circle having a diameter of approximately 12 mm. Moreover, the code, once stamped or impressed into the container, is preferably readable from the interior of the container.

Figure 8:
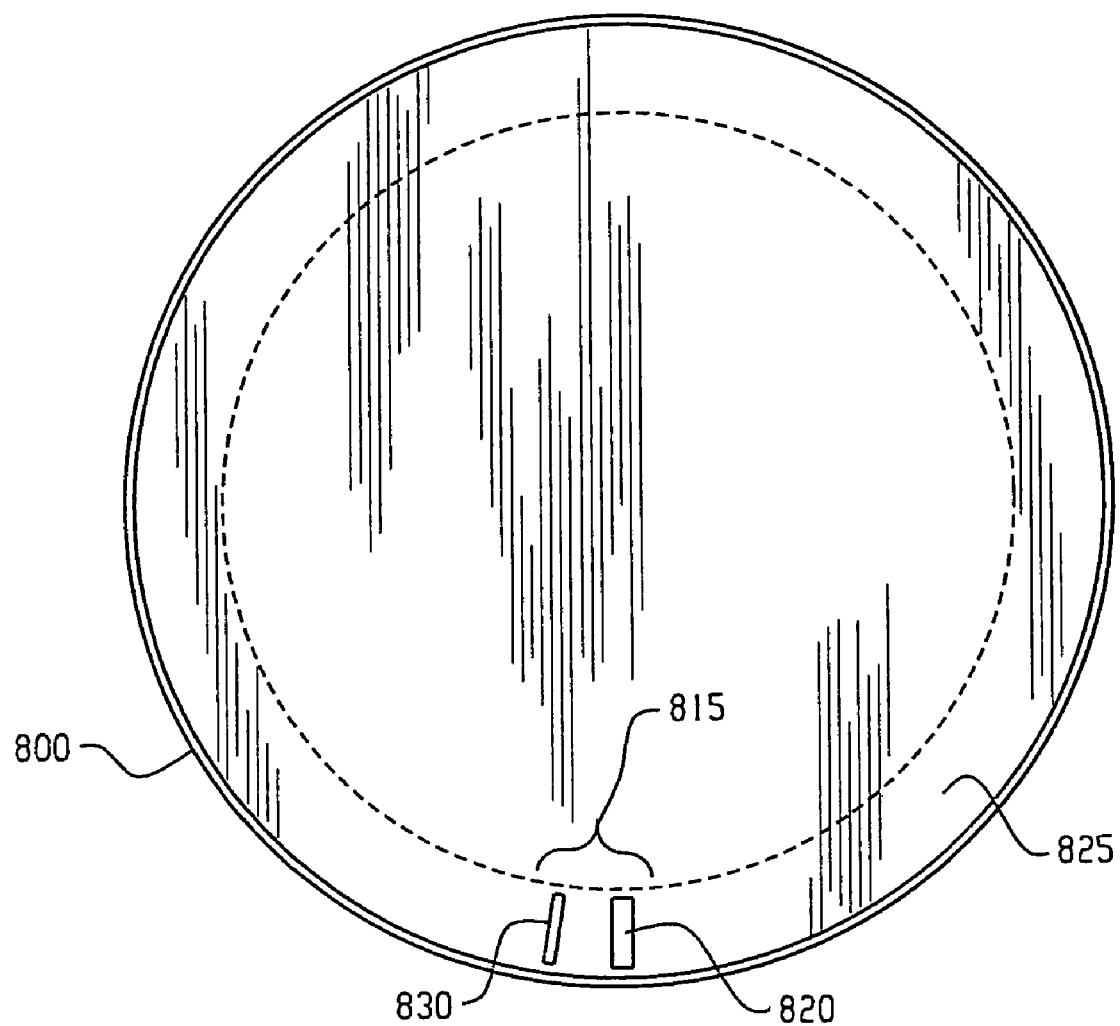
FIG. 8 is a diagram illustrating a punch having another example of a code according to the present invention.

FIG. 8 shows another candidate machine readable code 815 according to the present invention. The example code of this embodiment is shown as being formed in a doming punch 800. As with the previous embodiment, the code 815, or other codes, are formed on the doming punch in manners that will be apparent to those skilled in the art. It is to be understood that a doming punch is shown merely as an example. Other stamping and pressing hardware may also be implemented. Of course, it should be understood that such a doming punch (or other hardware) will typically be included within machinery to form metal containers. Whether or not to scale, the doming punch 800 has a code 815 formed in an area 825 that corresponds to a chime area of the bottom or base of a metal container. The code 815 shown is actually comprised of slots formed in the punch. This will result, as explained below, in a code impressed in the container that protrudes from the inner surface of the container. As a result, when the doming punch stamps the code in the container, the code is preferably located along the chime area of the base or bottom of the can. Moreover, the code, when stamped or impressed into the container, is preferably readable from the interior of the container. Typically the can is conveyed and transported by sitting upright on the can's normal bottom (tangent of the moat area). It is possible, however, that the material handling system is set up in a particular can manufacturer's plant to facilitate the easy viewing of the code on the outside of the can. Under such circumstance the invention can be practiced by making the necessary accommodations to facilitate this configuration.

As is illustrated, the code 815 impressed in the metal containers is comprised of a major mark 820 and a minor mark 830. The major mark 820 is used as a fiducial (or reference or orientation) element or mark to locate and orient the metal container during inspection. The minor mark 830 is used to identify the manufacturing path of the container based on its location relative to the major mark 820.

Using these exemplary schemes, up to 16 unique product codes can be produced as indicated in FIG. 1, or a number of codes, limited only by the space around the circumference of the base or bottom of the container, can be produced as indicated in FIG. 8. Of course, similar schemes could be used provided that a fiducial or reference marker to determine orientation of the container is included in any such similar code or a code may be used which does not require an orientation determination before reading. It should also be appreciated that the codes may vary with respect to human readability from application to application. In some circumstances, it may be preferred to use a code that is easily read and understood by humans, such as a code of a fiducial and a number of dots corresponding to a source of origin or path of manufacture. In other circumstances, the codes may be less readable by humans. It depends on the objectives of the users and the system. Designed in this fashion, the identifying code can be quickly deduced using modified algorithms that were originally designed primarily for defect attribute detection. Algorithms as described herein are well known in the art.

As noted, the codes, for example, as discussed in connection with FIGS. 1 and 8, are preferably formed in the containers so that the code is visible on the inside surface of the container but is less visible, or not visible, from the outside of the container. This approach is conducive to effective visual inspection of the inside of the container but does not significantly impact the aesthetics of the outside of the container. It should also be understood that there may be circumstances where it is desirable to have the code visible on the outside surface of the container. In this case, the code may or may not be visible from the inside of the container.

Typically, the system is operative to obtain an image of the container under inspection and, when determining the code, uses the fiducial to properly orient the image so that a proper comparison of the imaged code can be made to store information, or codes. With proper orientation and comparison, a manufacturing path or the source, of origin of an imaged container can be determined. It is an intention of this invention that an identifying code as indicated in FIG. 1 or 8 be stamped into the container as a surface relief attribute on the container bottom using press-specific dies. It should be appreciated that other known techniques for forming a surface relief code in a metal container surface may be used.

Figure 7:
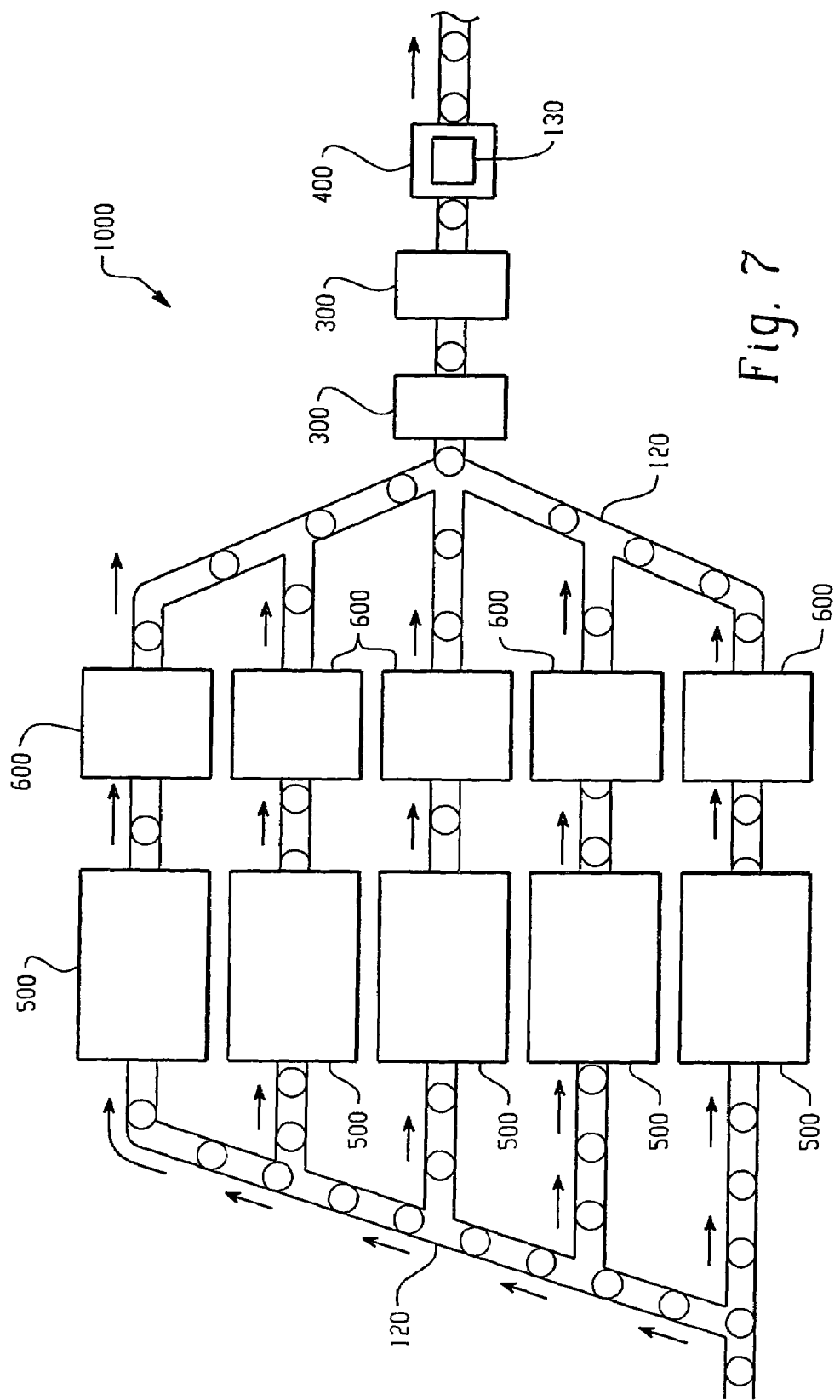
FIG. 7 is a block diagram of a system incorporating the present invention.

Referring now to FIG. 7, a manufacturing system for producing metal containers, stamping or impressing container codes within those containers, inspecting the containers to determine codes and defects, and associating those containers to paths of manufacturing or sources of origin based on the codes to generate quality status information is illustrated. More particularly, a system 1000 is shown wherein objects or containers are conveyed along paths shown at 120. As illustrated, these containers (or cups), in some form, are processed through body maker machines 500 and body trimmer machines 600 on a plurality of parallel paths, as is known. The containers are then merged onto a single path and processed through other processing machines 300 and, ultimately, provided to an inspection and/or imaging system 400 having an inspection zone 130. It is to be appreciated that the containers are stamped with a container code, such as those as shown in FIG. 1 or described in connection with FIG. 8, in the body maker machine 500. Preferably, the code is stamped in a location in the container such that the structural integrity and inspectability of the container is maintained such as, for example, the central base region in the domed area of the container or in the chime area circumferentially disposed about the base region. The chime area is comprised of metal at the original coil gauge and has not been worked such that strain hardening or thinning has occurred. It therefore is capable of withstanding the code without effecting the integrity of the metal or the strength of the container. The dies or doming punches (such as a doming punch 9) are modified, as shown in FIG. 1 or FIG. 8, by any known means, so that the appropriate code is pressed or stamped into the containers. This allows for the determination of the source of origin or the manufacturing path of the particular container to be identifiable at the inspection zone 130. Of course, the path of manufacturing and corresponding system components illustrated in FIG. 7 are merely illustrative and could otherwise take a variety of forms. For example, the number of operating body makers may vary substantially (e.g., from several to sixteen), depending on plant configuration and product needs.

Figure 2:
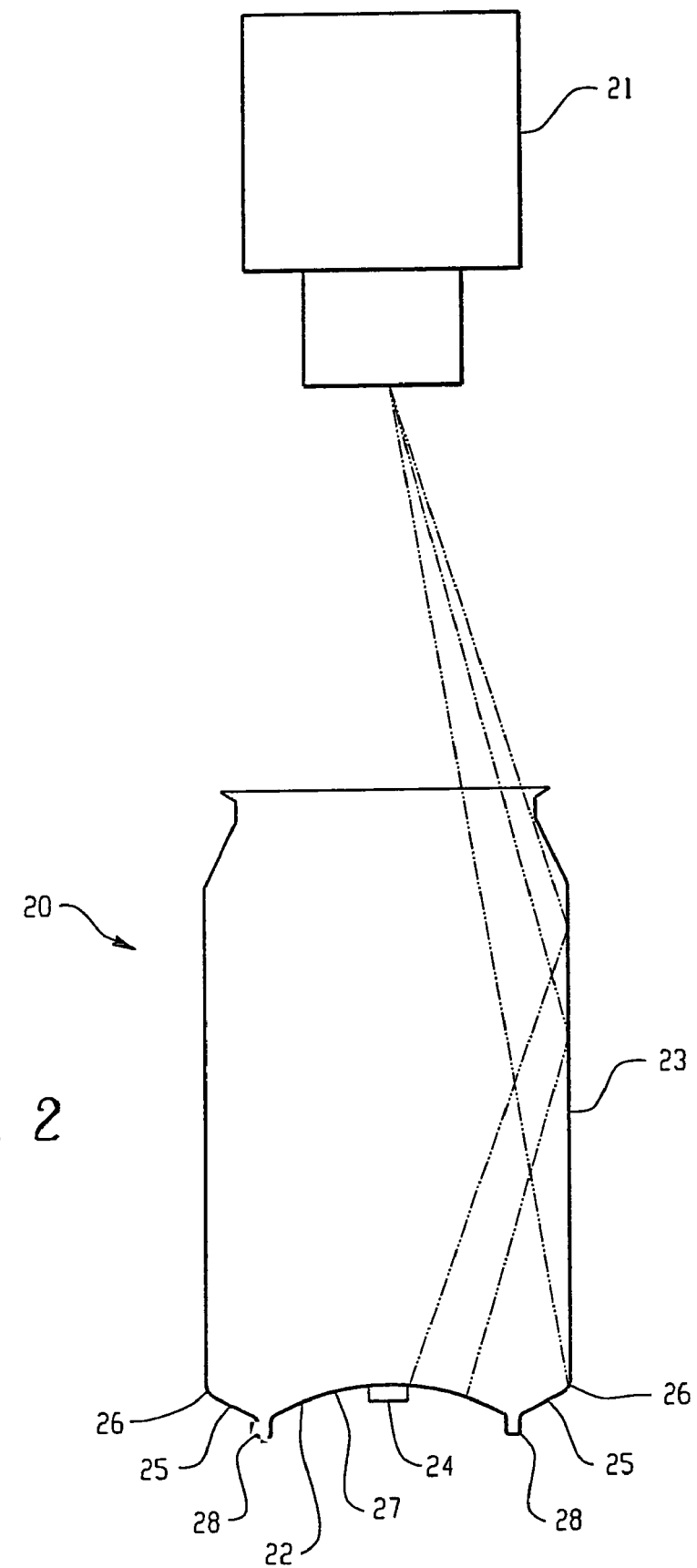
FIG. 2 is a diagram showing a cross-sectional view of a typical metal beverage container.

Referring to FIG. 2, the placement of a code, or container code, according to the present invention, would preferably be on the can bottom or base portion 22, in a small central base region 24 that is co-linear with the can axis or in the chime area 25 of the base of the container. Placed in these locations, the code attribute would interfere in a minimal fashion with the ability of the machine vision system to inspect the container for defect attributes. For completeness, the heel 26, domed area 27 and moat 28 are identified.

In this regard, the central base region 24 is preferably of a size so that illuminating the code does not create ghost images on the sidewall from disturbances to reflections of the illumination source that is illuminating through the opening of the container or can. In this case, preferably, the code is totally contained within an axially centered region in the dome of the bottom of the container which is circumscribed by a circle having a diameter of approximately 12 mm. FIG. 2 provides a schematic outline of a two-piece beverage can body 20 being imaged by an imaging lens/camera combination 21. Using this inspection configuration, which is typical of prior art deployments of automated container inspection systems, a region of zero base reflection off the container sidewall 23 is found in the central base region 24. Outside of the central base region 24 in the domed area of the base region, container attributes (both functional such as an identifying code, as well as defect attributes) show up in subsequent images of the sidewall 23 portion of the container 20. If allowed to overflow out of the central base region 24 within the domed area of the container 20, an identification code would begin to limit the signal-to-noise ratio associated with finding defect attributes in other regions of the can. Therefore, the ability of the machine vision system to inspect the container 20 in both the base region 22 (wherein the code was placed) as well as the sidewall region 23 would be adversely affected and would complicate or compromise the inspection process.

Additional incentives for locating an identifying code 10 in the central base region 24 of the container 20 is drawn from the fact that the central base region 24 is one of the least worked portions of the container in regards to metal deformation. As such, container defects rarely occur in this region of the container, thus reducing the need to perform defect attribute inspection in this region. Placement of an identifying code does not completely eliminate the ability to inspect the container in the region wherein the code is placed. By executing processing algorithms that compensate for the presence of the code attributes, it is possible to enact a degree of inspection not present in state-of-the-art container inspection systems. This improvement is achieved by having an image to inspect which is devoid of optical saturation in the area of the container central bottom, as is typical in state-of-the-art machine vision systems.

FIG. 2 also illustrates a chime area 25 that is circumferentially disposed around the base region of the container. The chime area 25 is disposed between the heel 26 and moat area 28 of the container. The side walls 23 extend from the heel 26 to the top of the container. The domed area 27 of the base region is surrounded by the moat area 28. Placement of the code in the chime area 25 (e.g., such as that described in connection with FIG. 8) can provide a good opportunity to image with strong visual contrast to the machine vision system and will be decodable by the system using a minimum of processing time. This type of placement will not significantly interfere with the ability of the machine system to detect defects that are present nor will it interfere with the form, fit or function of the container. It is also readable by humans in at least some forms and is inexpensive to retrofit into existing dome punches or dies. As such, placement of the code within the chime area 25 will not adversely effect or complicate or compromise the inspection process. In one form, the code is preferably placed near the moat area 28.

In addition, the chime area is another of the least worked portions of the container in regards to metal deformation. As such, sufficient material is typically present in the chime area to allow for formation of a code and container structural or forming defects rarely occur in this region of the container. Placement of an identifying code does not completely eliminate the ability to inspect the container in the region where the code is placed. By implementing processing algorithms that compensate for the presence of the code attributes, it is possible to enact a degree of inspection not present in state of the art container inspection systems. In one exemplary form, the implemented algorithm may identify marks that are actually defects based on size, location, number, . . . etc. This improvement is achieved by having an image to inspect which is devoid of optical illumination saturation in the chime area as is typical in state of the art machine vision systems.

Figure 9A:
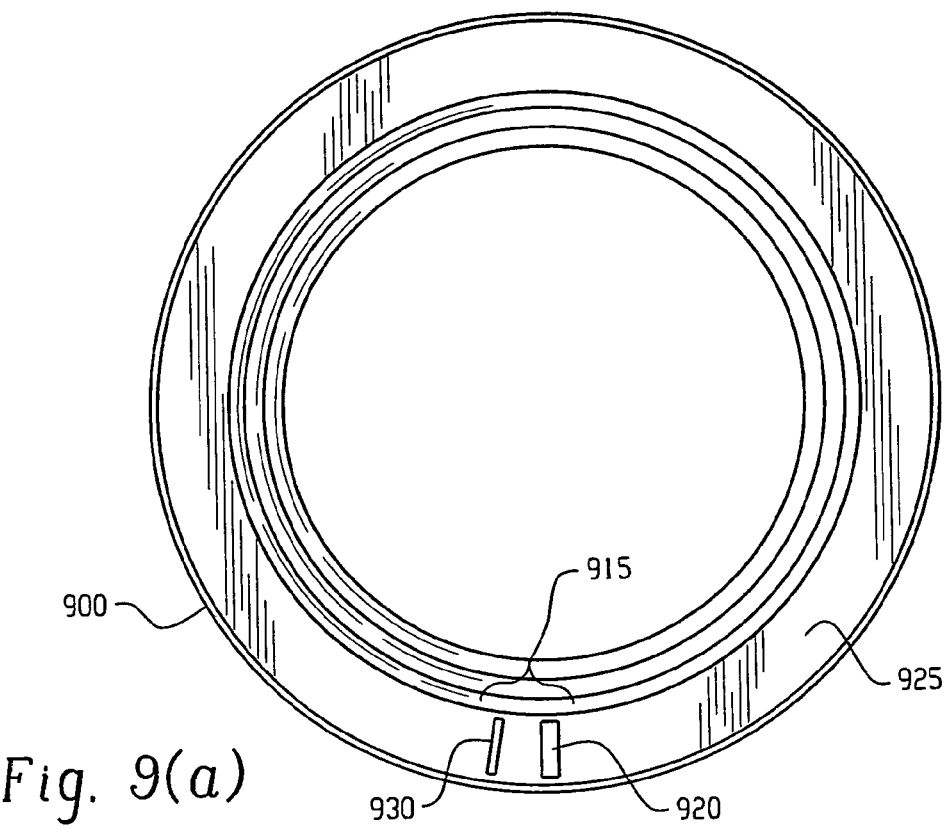
FIG. 9(a) is an illustration showing a container having a code according to the present invention formed therein.
Figure 9B:
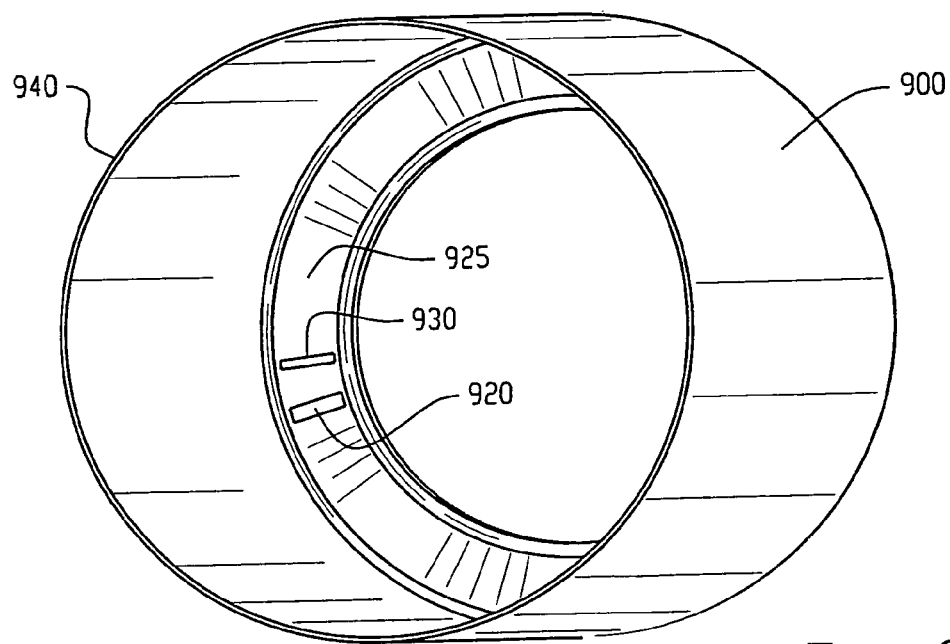
FIG. 9(b) is an illustration showing a container having a code according to the present invention formed therein.
Figure 10:
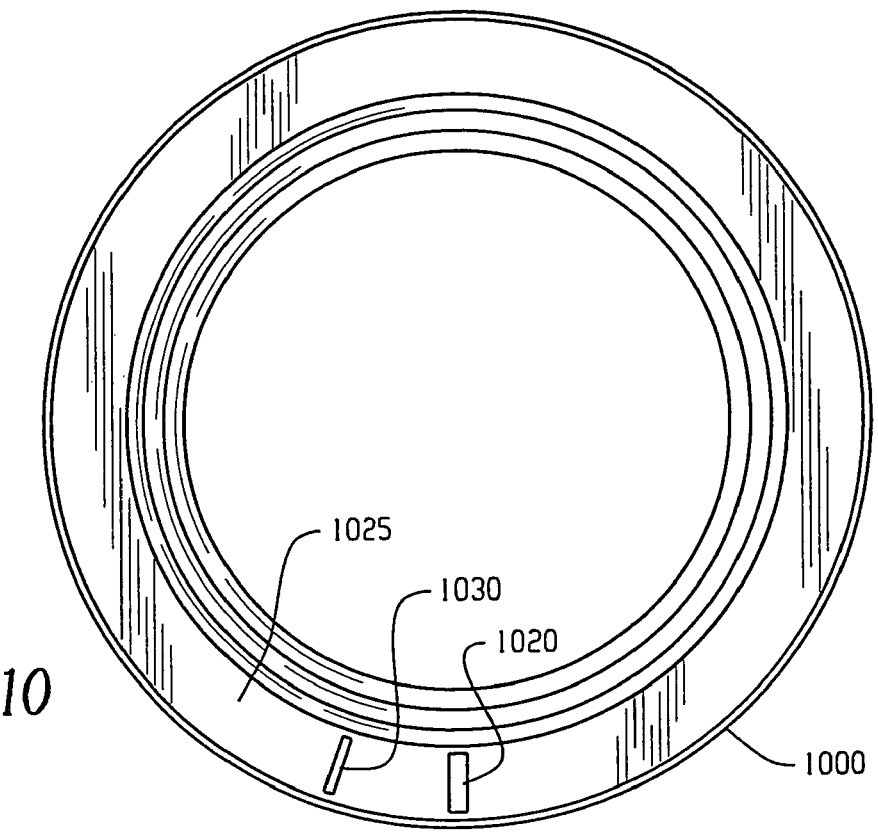
FIG. 10 is an illustration showing a container having a code according to the present invention formed therein.
Figure 11:
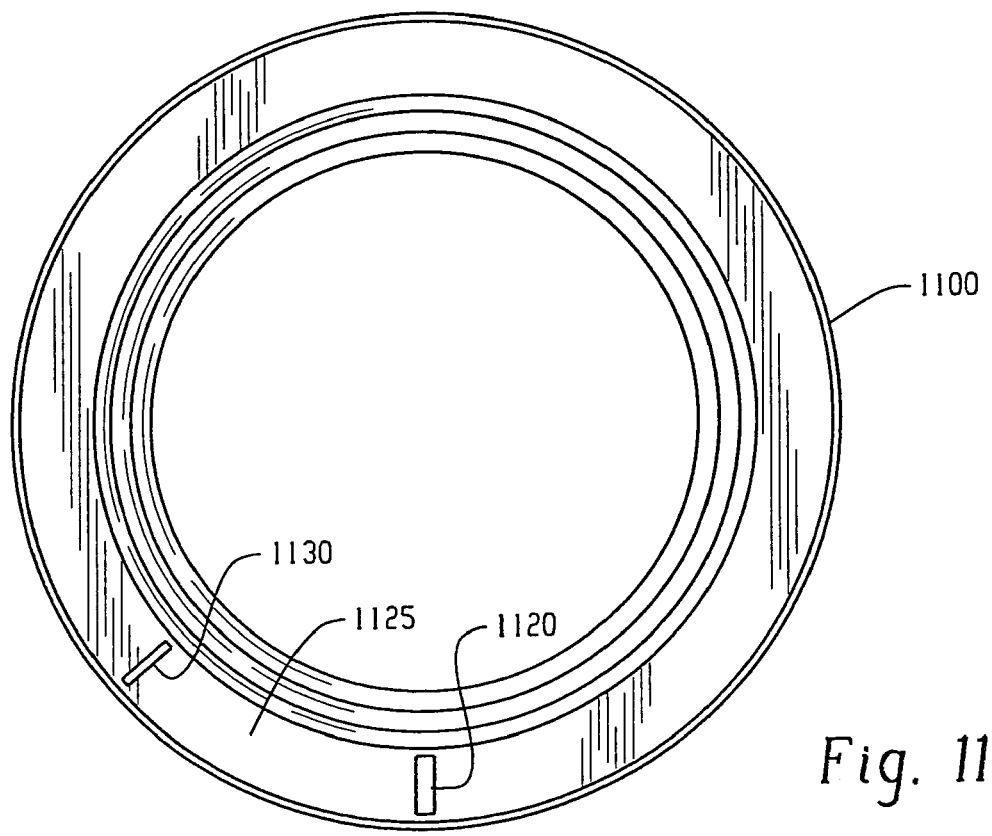
FIG. 11 is an illustration showing a container having a code according to the present invention formed therein.
Figure 12:
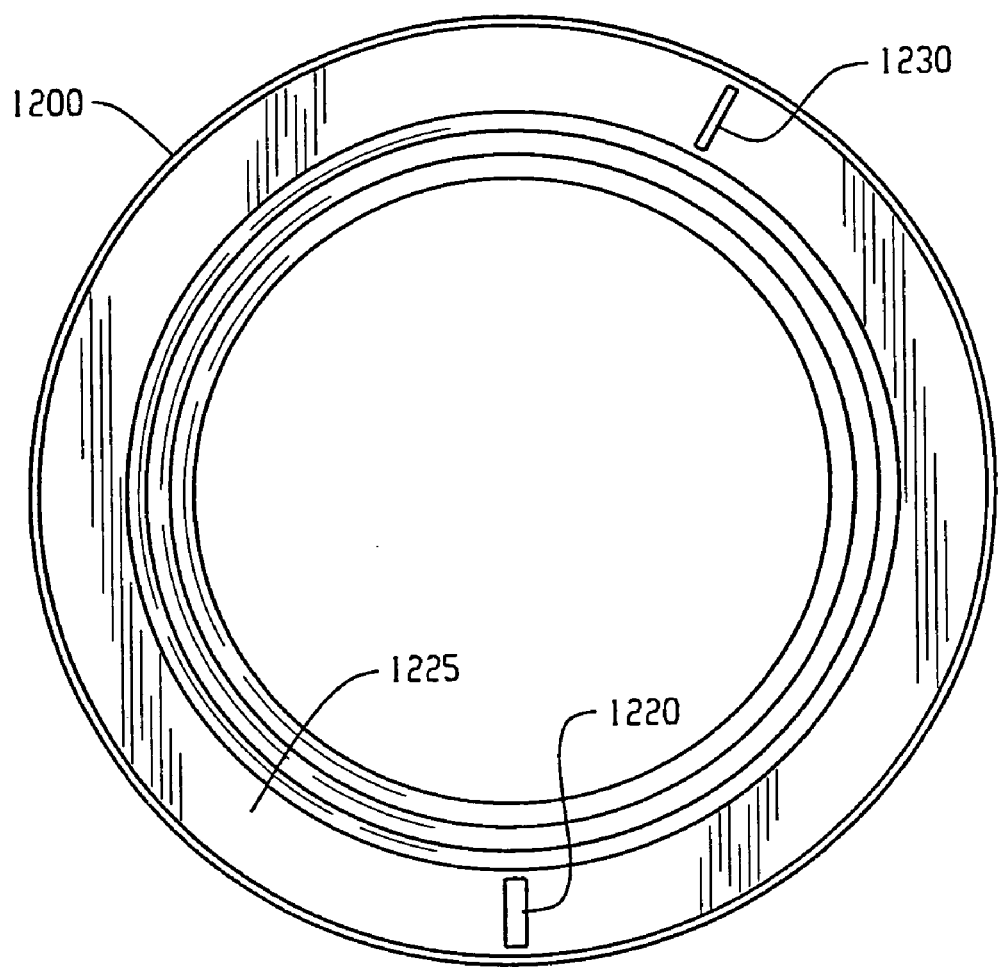
FIG. 12 is an illustration showing a container having a code according to the present invention formed therein; and, FIGS. 13(*a*), (*b*) and (*c*) are illustrations showing a container having a code according to the present invention formed therein.

To illustrate the implementation of the dome punch 800, FIGS. 9(*a*) and 9(*b*) illustrate a container 900 showing a major mark 920 and a minor mark 930. FIG. 9(*b*) also shows side walls 940. Of course, the code (shown collectively as 915) is illustrated as being contained within a chime area 925 of the container 900. This placement results in the advantages noted above. It should also be noted that the code configuration shown in FIGS. 9(*a*) and 9(*b*) is only an example. In this regard, a variety of codes, the number of which is limited only by the space available around the circumference of the container bottom, may be implemented. Other examples are illustrated in FIGS. 10, 11 and 12. In this regard, FIG. 10 shows a metal container 1000 having a major mark 1020 and a minor mark 1030. These marks are contained within the chime area 1025. Likewise, FIG. 11 shows a container 1100 having major mark 1120 and minor mark 1130 contained within a chime area 1125. Still further, FIG. 12 illustrates a container 1200, having within its chime area 1225, a major mark 1220 and a minor mark 1230. As can be seen from these figures, the implementation of varying codes based upon a fiducial mark or major mark, and the relative position of a minor mark, can be used to identify the manufacturing path of the container.

Figure 13A:
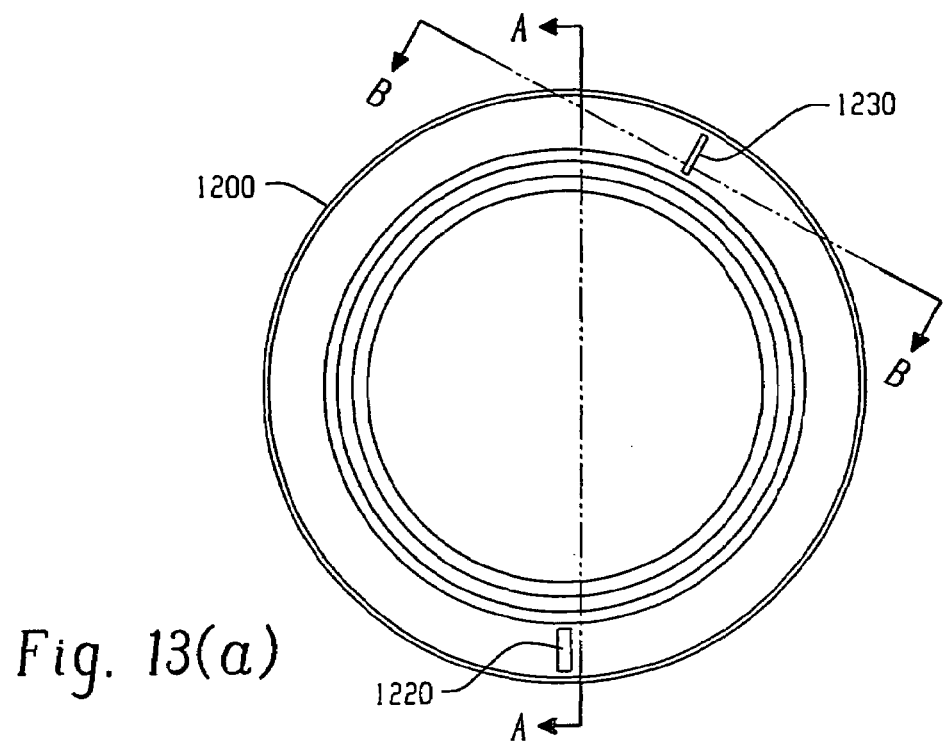
Figures 13B, 13C:
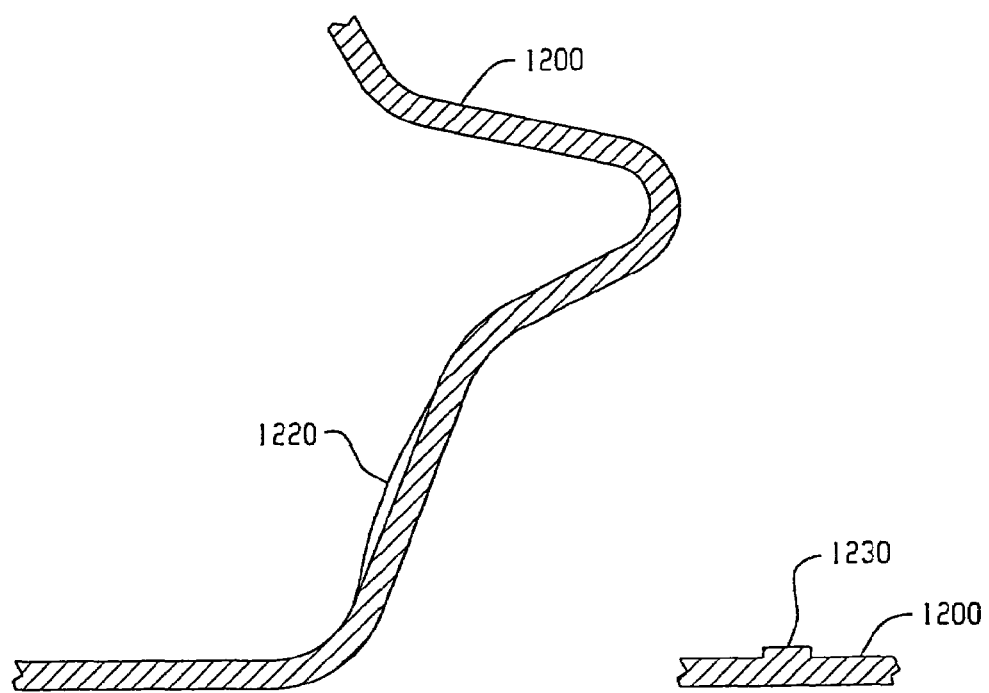

As noted above, one of the preferences of the present invention is to use marks that are visible from the inside of the container. It is also preferable if the marks are not visible (or only slightly visible) from the outside of the container. With reference now to FIGS. 13(*a*)–(*c*), this feature is shown with respect to the codes shown in FIGS. 8, 9(*a*), 9(*b*), 10, 11 and 12. Of course, it should be understood that a process similar to that described below could be used for codes placed in other areas of the base of the container, such as the center of the domed area (as discussed in connection with FIG. 1.

In FIG. 13(*a*), the container 1200 is illustrated. The major mark 1220 and minor mark 1230 are shown. With reference to FIG. 13(*b*), it is apparent that the mark 1220 protrudes from the inner surface of the container 1200. However, it is understood that it does not protrude from the outer surface. Likewise, the mark 1230 is shown in FIG. 13(*c*) as protruding from the inner surface, but not from the outer surface. Indeed, the outer surface has little or no indication that a mark was formed on the inner surface.

In one example form, the components protrude approximately 0.01 inches from the surface at their maximum height. The minor marks may also have a width approximately 0.031 inches. The major marks may have a width of approximately 0.063 inches. Of course, the dimensions are merely illustrative and should not be construed as limiting. The length of the marks should be selected based on the dimensions of the chime area, the tooling used, customer acceptability, inspection system resolution etc. As shown, the marks have a curve therein as a result of the formation of a curved slot in the corresponding dome punch.

Formation of codes (as described herein or others) is accomplished during the formation process in the body maker (such as a body maker machine 500 illustrated in FIG. 7). In this regard, very high air pressure is typically created when forming the metal container. As the container is formed, the ironing/doming punch irons out the walls of the container to the base portion wherein air is trapped, creating the high air pressure. This air pressure pushes metal into the slots of the punch to stamp or impress or create the code on the inner surface of the container. However, the air pressure is not typically of sufficient magnitude to create as significant an indication on the outer surface of the container thus making the code less noticeable on the outside. Of course, the process could be altered to obtain a different result, e.g., to have the code more visible on the outside surface of the container, if desired.

Figure 3:
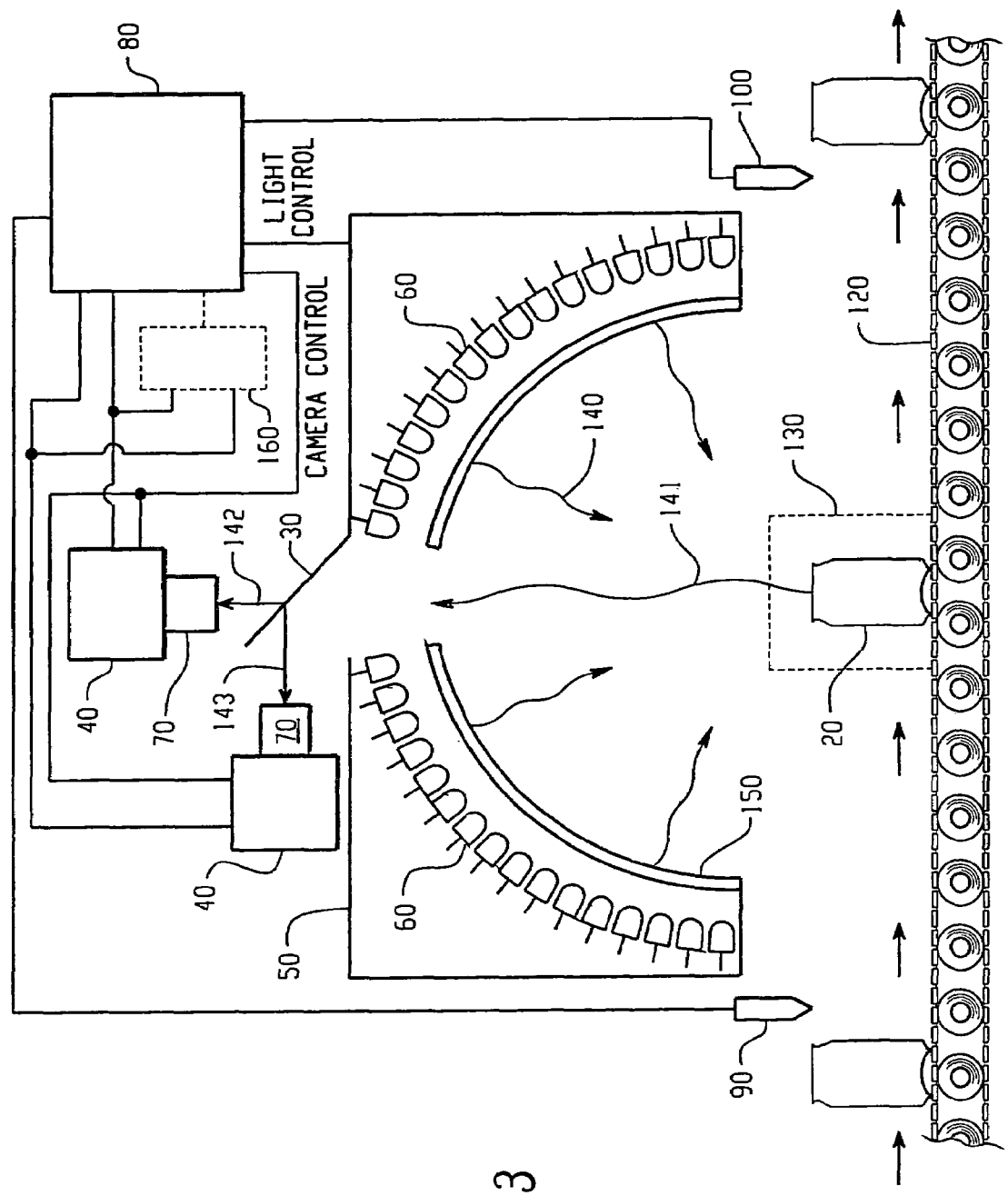
FIG. 3 is a block diagram illustrating a machine vision system according to the present invention.

FIG. 3 provides a schematic outline of a preferred embodiment of the disclosed invention. In FIG. 3, a container 20 (having a container code appropriately placed thereon using a variety of known techniques, including those mentioned herein, to indicate its original body maker or press of origin) undergoing inspection is transported into an inspection zone 130 via some means of object conveyance 120. It should be understood that the container 20 may include a code 10, the codes described in connection with FIGS. 8, 9(*a*), 9(*b*), 10, 11, 12 or 13(*a*)–(*c*), or other codes contemplated herein. There are various types of part or object conveyor systems that have been constructed and are well known in the art. When the container 20 to be inspected is within the inspection zone 130, a spectrally and spatially configurable illumination field 140 is generated by the solid-state illuminator 50 and directed onto the container 20. The solid-state illuminator 50 is constructed out of an array of individual LED's 60. Placed physically together within the solid-state illuminator 50, it is possible to generate a large variety of output illumination fields 140. By varying the number and type of LED's 60, the various drive currents supplied to the LED's 60, or the pulse duration applied to the LED's, illumination fields 140 of infinitely configurable content can be produced via the linear superposition of the individual LED spectra. The illuminator 50 implemented in the embodiments described (e.g. FIGS. 3, 4 and 5) includes in at least some forms solid state illumination arrays and is positioned to illuminate the interior of the container. Preferably, reflected illumination is used to implement the system.

Also included within the preferred embodiment of the solid-state illuminator is a diffuser 150. The diffuser 150 homogenizes the emitted illumination fields 140 in regards to their spatial uniformity. In many automated measurement or inspection applications, spatially uniform illumination fields 140 are required for optimum system operation.

In the preferred embodiment of the disclosed invention, the LED's are deployed in a three-dimensional shape approximating a hemisphere. This shape of illuminator is well known in the art having the properties of generating highly uniform isotropic illumination. This type of illumination is preferred for many classes of inspection or measurement applications. However, other LED array configurations such as flat panel arrays or annular ring lights find useful application in other cases. The spirit of the invention includes the implementation of the solid-state illuminator 50 using these alternate physical configurations.

After reflecting off of the container 20 under inspection, reflected light 141 is directed first in the direction of the solid-state illuminator 50 and on through to a beam splitter 30. The beam splitter 30 is used to selectively direct the reflected light into 2 different images or channels. One image or channel is the defect attribute image or channel 142 while the other image or channel is the container code image or channel 143. Beam splitters 30 as indicated herein are well known in the art, being deployed in a variety of state-of-the-art machine vision systems for a variety of reasons. Such beam splitters 30 can be designed and manufactured with a variety of reflection/transmission specifications. It is typical in many machine vision systems to use a 50/50 beam splitter design. With a 50/50 beam splitter, half of the incident light or energy is transmitted through the beam splitter while the other half of incident light is reflected off the incident surface. In the preferred embodiment, it is envisioned that the ideal beam splitter construction would differ from a 50/50 device. When illuminated from above as indicated in FIG. 3, the reflected illumination fields associated with metal food or beverage container are very non-uniform as a function of container radius. There is an order of magnitude difference in the reflected intensity as one moves about along the inside can surface. More specifically, the reflections coming from the container bottom, located normal to the optical axis of the system are very strong. In contrast, the amount of light glancing off of the container sidewalls in the direction of the optical axis of the imaging system is quite low. As such, different illumination exposure levels necessarily need to be used for the defect attribute image or channel 142 as compared to the container code image or channel 143 in order that the container code image or channel 143 be acquired out of optical saturation. To this end, it is envisioned that a higher percentage of incident illumination will need to be directed by the beam splitter 30 in the direction of the defect attribute image or channel 142. Beam splitter ratios of 70/30 or 80/20 are likely to be used in the preferred embodiment.

Returning to FIG. 3, two imaging lens 70/camera 40 combinations are used to receive light reflecting off the container 20 under test. The type of imaging lens 70 used in the disclosed invention is well known in the art. In general, the imaging lens 70 needs to operate within the visible spectrum and be able to form an image of an object or a scene at its back focal plane.

In the preferred embodiment, both cameras 40 (the one associated with the defect attribute channel 142 and the one associated with the container code channel 143) send image data to an image processor 80. Alternately, based on the discretion of the implementers, the two image signals produced by the cameras 40 can be directed to a video multiplexing module 160 that acts to electronically combine the two independent video streams into a single compound video channel. Video multiplexers 160 as described herein are well known in the art. By multiplexing the defect attribute image 142 and the container code image 143 into a single video channel, the cost of a suitable machine vision system capable of identifying and associating container defects to the body maker or machinery of origin can be further reduced.

In the preferred embodiment, the image processor 80 receives a signal from a part presence mechanism 90 that indicates to it that a container 20 is about to pass through the inspection zone 130. Part presence mechanisms 90 such as photo-eyes are well known in the art and are deployed in many applications within many different industries. After performing some time-based or movement-based timing operations designed to accurately place the dynamic container 20 in the exact center of the inspection zone 130, the image processor 80 issues control signals to both cameras 40 and the solid-state illuminator 50. These signals are used to enable the acquisition of both defect attribute and container code information. Once processing operations on the raw data have been completed and the quality status of the container 20 has been determined, a signal is issued by the imaging processor 80 to a status enunciator 100. The status enunciator 100 could be implemented as a rejector that physically removes parts determined to be below, or alternately above, a predetermined quality standard. Alternately, the status enunciator 100 could be implemented as a type of audio or visual warning signal indicative of part quality.

In the case of machine vision systems that are capable of accumulating quality status information as a function of machine manufacturing path or machine entities, the presentation of the correlated quality status report is preferably presented in the graphical or tabular form. In these cases the preferred embodiment of the status enunciator 100 is either a graphical display monitor such as a LCD or CRT monitor.

Alternately, the status indicator could be implemented as printer device capable of generating printed hardcopy reports of the correlated quality status reports. The ability to graph current or historical defect rates as a function of machine entity is a primary output of this class of machine vision system in addition to the fundamental notification or rejection of defective containers.

Figure 4:
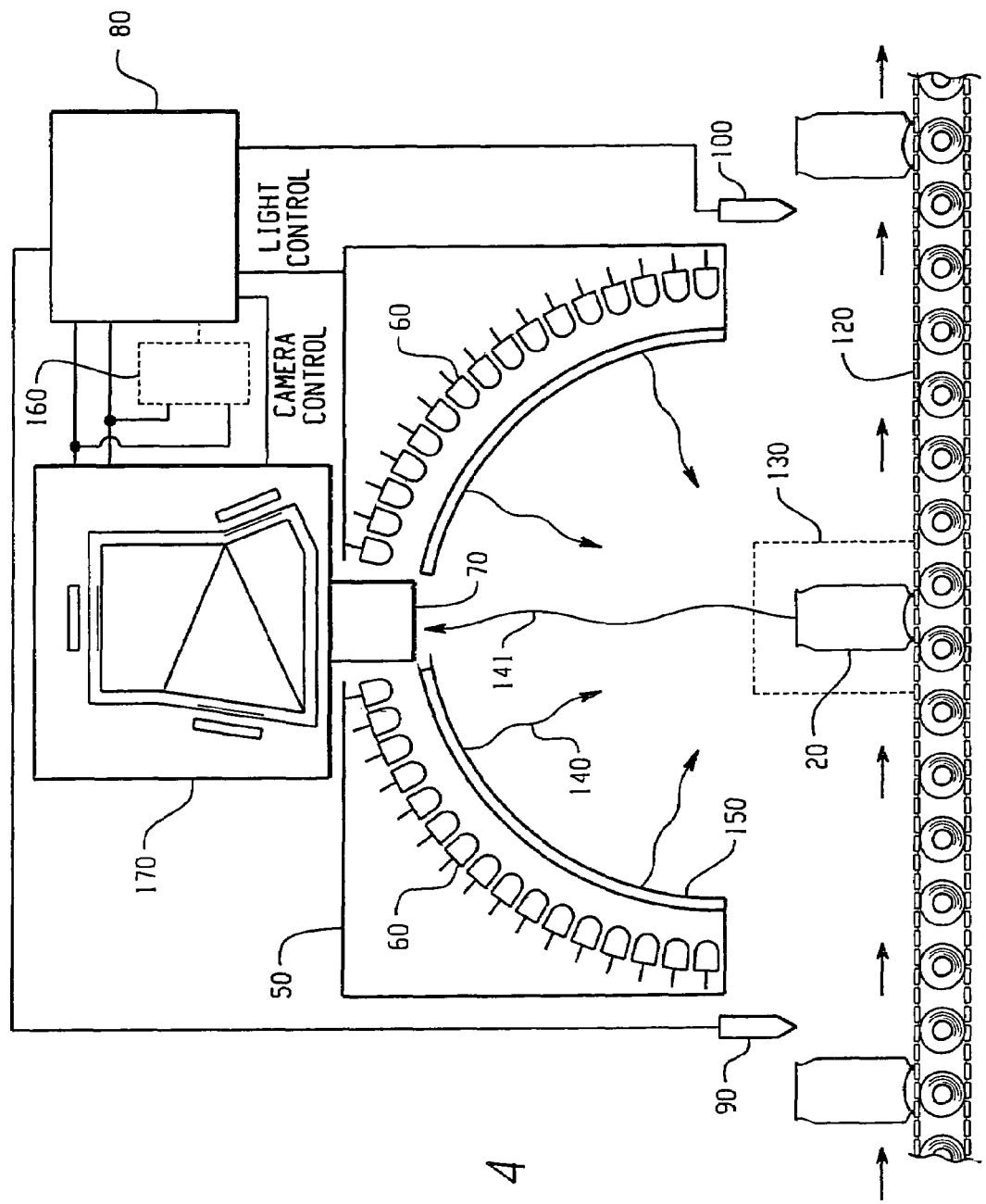
FIG. 4 is a block diagram illustrating an alternate implementation of a machine vision system according to the present invention.

FIG. 4 provides a schematic outline of an alternate embodiment of the disclosed invention. In this implementation, a multi-channel camera 170 is used to obtain both the defect attribute and container code image information. Multi-channel cameras are well known in the art (typically implemented as Red/Green/Blue RGB cameras). Cameras of this type use spectral filtering techniques within the camera housing to separate the received image information into multiple video channels. By carefully configuring the images of the multi-channel camera 170 in coordination with the solid-state illuminator 50, it is possible to simultaneously receive within a multichannel camera 170 both a defect attribute image as well as a container code image. These two images are then routed to an image processor 80 or, alternately, a video multiplexing module 160 as described previously.

Figure 5:
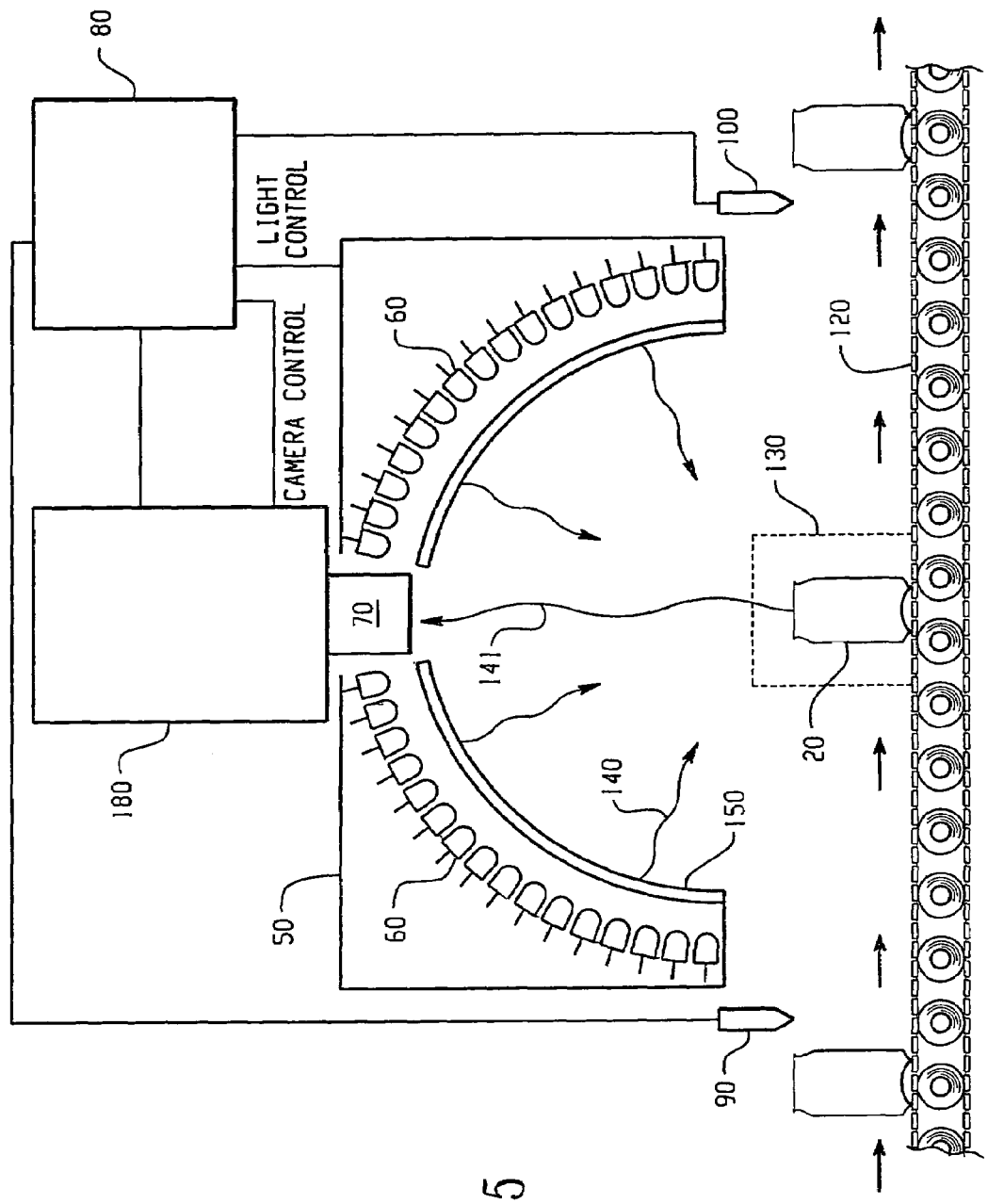
FIG. 5 is a block diagram illustrating yet another alternate implementation of a machine vision system according to the present invention.

FIG. 5 provides a schematic outline of yet another alternate embodiment of the disclosed invention. In this implementation, a single, high-speed camera 180 is used in conjunction with an imaging lens 70 to sequentially acquire both a defect attribute image and a container code image for each container 20 that passes through the inspection zone 130. High scan rate cameras 180 as discussed herein are well known in the art. Specifically, CMOS imagers are commercially available that support the integration and clocking-out of image data within 2 milliseconds. Image acquisition speeds of this magnitude support the prospect of capturing 2 independent images for the same part using the same camera 180 as the part passes dynamically through the inspection zone 130. CMOS imagers support configurable signal integration times that can be changed on the fly. This, in combination with on-the-fly configurable solid-state illumination support the acquisition of both a preferred defect attribute image as well as an out of saturation container code image without requiring the use of filters or beam splitters.

Figure 6:
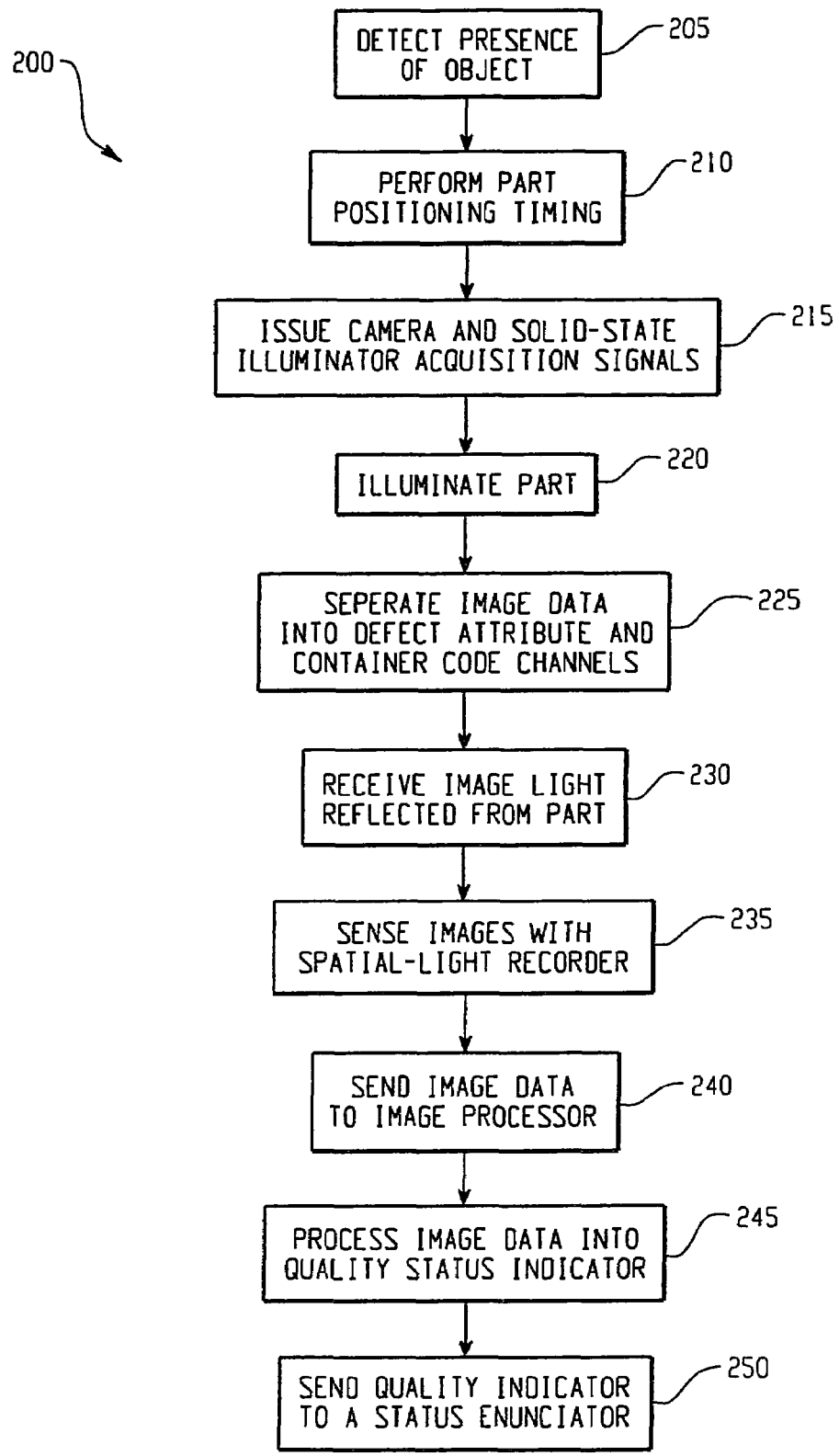
FIG. 6 is a flow chart illustrating a machine vision method according to the present invention.

Referring now to FIG. 6, one preferred automated inspection method 200 reflecting the basic steps of operation is shown. It should be understood that the containers that are contemplated for inspection under the teachings of the present invention are formed with the container code included in a surface thereof using any of a variety of techniques that are well known, including those specifically mentioned herein. The forming of the code in the surface of the container occurs prior to the container being conveyed into the inspection zone. Once conveyance begins, the container under test (and having the container code thereon) is eventually detected approaching an inspection zone 130 (step 205). The image processor 80 performs detailed time or movement-based positioning of the container under test to place it in the center of an inspection zone 130 (step 210). The image processor 80 then sends control signals to the cameras 40 associated with both the defect attribute data and the container code data as well as to the solid-state illuminator 50. This starts the image acquisition process (step 215). In response to the control signals applied by the image processor 80, the solid-state illuminator 50 acts to illuminate the container under test with illumination fields (step 220). Preferably, the light originates in an area near the lens of the imaging system to provide reflected illumination of the interior of the container (e.g. front lighting as opposed to transmissive backlighting). Light reflecting 141 off the container under test is then separated into 2 channels, the defect attribute channel and the container code channel, by a beam splitter 30 (step 225). The reflected image data associated with both the defect attribute channel as well as the container code channel is received by an imaging lens 70 (step 230). Two images are simultaneously formed by suitable spatial light recorders contained within the system's cameras 40 (step 235). Image data obtained by the cameras 40 are sent to an image processor 80 (step 240). The image processor 80 processes the raw data into quality status information related to the container under test (step 245). Included in the status information related to the container under test is data relating part quality to the specific body maker, press, trimmer or other machinery that formed the part, based on the container code of the part. Finally, the image processor 80 sends the quality status information related to the container under test to a status enunciator 100 (step 250).

Of course, it should be appreciated that similar methods using the systems described in connection with FIGS. 4 and 5 are contemplated. Such methods may vary slightly from that described in connection with FIG. 6. For example, steps 225, 230, 235 and 240 may well be modified or replaced with steps designed to allow cameras 170, 180 to receive reflected light and appropriately provide data to the processor 80 (consistent with that which is described in connection with FIGS. 4 and 5). It should be further appreciated that all such methods (and the corresponding systems) according to the present invention may be implemented using a variety of software techniques and hardware implementations that will vary from implementation to implementation.

It should be recognized that a system to perform the inspection and identification as herein described could comprise a single processor or separate multiple processors which have been configured and programmed to communicate the relevant results between them. It still can be regarded as a "system" as specified herein.

While particular embodiments have been described, alternatives and/or substantial equivalents may become apparent to those skilled in the art. The invention described herein encompass all such embodiments.

We claim:

1. A system comprising:
    a conveyor operative to convey a metal container having a code formed in a chime area surface thereof, the code being unique to a path of manufacturing of the metal container;
    an inspection zone into which the metal container is conveyed;
    an illuminator operative to illuminate the metal container in the inspection zone;
    at least one imaging system operative to acquire information on defects and the code; and,
    at least one processor operative to process the information on the defects and the
    code to generate quality status information relating quality of the metal container to the path of manufacturing of the metal container.

2. The system as set forth in claim 1 wherein the code is formed to be visible on an inside surface of the container and less visible on an outside surface of the container.

3. The system as set forth in claim 1 wherein the code is formed in the container by a body maker.

4. The system as set forth in claim 1 wherein the imaging system is operative to inspect the defects at a first exposure level and to inspect the code at other exposure levels.

5. The system as set forth in claim 1 wherein the imaging system comprises at least one beam splitter, used with lenses and cameras to determine defects and the code by separating reflected light generated by the illuminator into at least two separate images.

6. The system as set forth in claim 1 wherein the imaging system uses spectral filtering to separate a received image into multiple video images.

7. The system as set forth in claim 1 wherein the imaging system comprises a high speed camera and a lens to sequentially acquire a defect attribute image and a code image.

8. The system as set forth in claim 1 wherein the imaging system is comprised of more than one camera to image the defect uniquely from the code.

9. A method for inspecting metal containers, the method comprising:
    stamping a code in a chime area surface of a metal container, the code being unique to a path of manufacturing of the metal container;
    conveying the metal container into an inspection zone;
    illuminating the metal container in the inspection zone;
    inspecting the metal container to determine defects in the container;
    inspecting the metal container to determine the code; and,
    accumulating quality status control information based on the defects and the code.

10. The method as set forth in claim 9 wherein the stamping comprises forming the code in the chime area surface such that the code is visible on an inside surface of the container and less visible on an outer surface of the container.

11. The method as set forth in claim 9 wherein the stamping comprises using press-specific die sets.

12. The method as set forth in claim 9 wherein inspecting the metal container for defects comprises inspecting at a first illumination exposure level and inspecting the metal container for the code comprises inspecting at a second illumination exposure level.

13. The method as set forth in claim 9 wherein the inspecting of the container for defects and the inspecting of the container for the code comprises using spectral filtering to separate a received image into multiple video images for subsequent processing.

14. The method as set forth in claim 9 wherein the inspecting to determine defects and the inspecting to determine the code comprises using a high-speed camera and a lens to sequentially acquire a defect attribute image and a code image.

15. The method as set forth in claim 9 wherein the inspecting to determine defects and the inspecting to determine the code comprise separating reflected light resulting from the illuminating into two separate channels using a beam splitter.

16. The method as set forth in claim 9 wherein the stamping comprises using a body maker.

17. A system for inspecting metal containers, the system comprising:
   means for impressing a code into a chime area surface of a metal container, the code being unique to a path of manufacturing of the metal container;
   means for conveying the metal container into an inspection zone; means for illuminating the metal container which is in the zone; means for inspecting the metal container to determine defects in the container and to determine the code; and,
   means for accumulating quality status control information based on the defects and the code.

18. The system as set forth in claim 17 wherein the means for illuminating the metal container is comprised of solid state illumination array(s) and illuminates the interior of the container.

19. The system as set forth in claim 17 wherein the means for stamping comprises a press-specific die set implemented within a body maker.

20. The system as set forth in claim 17 wherein the means for inspecting comprises means for inspecting at a first illumination exposure level to determine defects and a second illumination exposure level to determine the code.

21. The system as set forth in claim 17 wherein the means for inspecting comprises means for providing spectral filtering to separate a received image into multiple video images.

22. The system as set forth in claim 17 wherein the means for inspecting comprises a high-speed camera and a lens to sequentially acquire a defect attribute image and a code image.

23. The system as set forth in claim 17 wherein the means for inspecting comprises a beam splitter for separating reflected light into two separate images.

* * * * *